(12) United States Patent
Alawa (10) Patent No.: US 10,448,822 B2
(45) Date of Patent: Oct. 22, 2019

(54) METHOD AND SYSTEM FOR VISUAL FIELD PERIMETRY TESTING USING A HEAD-MOUNTED DISPLAY ASSEMBLY

(71) Applicant: Karam AlRahman Alawa, Miami, FL (US)

(72) Inventor: Karam AlRahman Alawa, Miami, FL (US)

(*) Notice: Subject to any disclaimer, the term of this patent is extended or adjusted under 35 U.S.C. 154(b) by 0 days.

(21) Appl. No.: 15/880,925

(22) Filed: Jan. 26, 2018

(65) Prior Publication Data

US 2019/0231184 A1 Aug. 1, 2019

(51) Int. Cl.
*A61B 3/00* (2006.01)
*A61B 3/024* (2006.01)
*H04W 88/02* (2009.01)

(52) U.S. Cl.
CPC ............ *A61B 3/005* (2013.01); *A61B 3/0033* (2013.01); *A61B 3/024* (2013.01); *G09G 2320/0693* (2013.01); *H04W 88/02* (2013.01)

(58) Field of Classification Search
CPC ....... A61B 3/024; A61B 3/0091; A61B 3/032; A61B 3/0033
USPC ........................................................ 351/224
See application file for complete search history.

(56) References Cited

U.S. PATENT DOCUMENTS

| | | | |
|---|---|---|---|
| 5,737,060 A | 4/1998 | Kasha, Jr. | |
| 8,132,916 B2 | 3/2012 | Johansson | |
| 9,578,318 B2 * | 2/2017 | Fleck | .................. H04N 13/296 |
| 2007/0200927 A1 | 8/2007 | Krenik | |
| 2011/0273670 A1 * | 11/2011 | Tsuta | .................. A61B 3/0091 |
| | | | 351/224 |
| 2016/0062454 A1 | 3/2016 | Wang et al. | |

OTHER PUBLICATIONS

"Detecting Glaucoma With a Portable Brain-Computer Interface for Objective Assessment of Visual Function Loss", Masaki Nakanishi, PhD et al., JAMA Ophthamology, Jun. 2017, vol. 135, No. 6, pp. 550-557.
"Visual Field Examination Method Using Virtual Reality Glasses Compared with the Humphrey Perimeter", Stylianos Tsapakis et al., Clinical Ophthalmology 2017:11 pp. 1431-1443.

* cited by examiner

*Primary Examiner* — Mohammed A Hasan
(74) *Attorney, Agent, or Firm* — Gordon & Jacobson, P.C.

(57) ABSTRACT

An improved visual field perimeter testing tool is provided that employs a head mounted display apparatus configured to removably support a hand-held electronic device comprising at least one processor, memory system and integral display screen. The memory system stores a software program executed by the at least one processor, wherein execution of the software program carries out visual field perimeter testing of a subject wearing the head-mounted display apparatus whereby discrete stimuli are presented to the subject on the display screen of the hand-held electronic device. In order to address nonlinearity of the display characteristics of the hand-held electronic device, a calibration routine can be performed to generate calibration data that is stored as part of the software program and used to generate the RGB pixel values for the discrete stimuli and background that surrounds the discrete stimuli in a manner that provides accurate contrast sensitivity measurements during the testing.

28 Claims, 8 Drawing Sheets

METHOD AND SYSTEM FOR VISUAL FIELD PERIMETRY TESTING USING A HEAD-MOUNTED DISPLAY ASSEMBLY

BACKGROUND

1. Field

The present disclosure relates to tools and methods of visual field perimetry testing, specifically to the use of head-mounted display technology in visual field perimetry testing.

2. State of the Art

Automated perimetry testing is a useful method to assess visual fields for screening, monitoring and assisting in the diagnosis of certain ocular conditions, such as glaucoma and some macula, retinal and neuro-ophthalmic conditions. The normal field of vision encompasses approximately 50 degrees nasal and superior, 70 degrees inferior, and 90 degrees temporal. Sensitivity is greatest in the middle and declines toward the periphery, commonly referred to as the "hill of vision." A visual field condition or defect can be considered to be any significant change in sensitivity from this normal hill of vision.

Various testing modalities are currently available for assessing visual fields. Frequency doubling technology (FDT) perimetry testing is based on a flicker illusion created by counterphase flickering of a low spatial frequency sinusoidal grating at a high temporal frequency. This phenomenon essentially creates an image that appears double its actual spatial frequency.

There are two generations of FDT perimeter testing tools sold commercially, including a first FDT perimetry testing tool sold commercially by Welch Allyn of Skaneateles, N.Y. and a second generation FDT perimetry testing tool referred to as the Humphrey Matrix tool sold commercially by Carl Ziess Meditec, Inc. of Dublin, Calif. Both generations of machines are portable and can be set on a flat table-top surface at sitting level for use.

The first generation FDT perimeter testing tool employs two different presentation patterns, which are referred to as a C-20 pattern and N-30 pattern. The C-20 pattern incorporates seventeen different points within a central 20-degree radius (i.e., four targets in each quadrant and one central target), while the N-30 pattern incorporates two additional nasal targets above and below the horizontal meridian. Both test patterns can be used in screening or threshold testing. Good sensitivity and specificity for detecting glaucomatous change has been described using both screening and threshold testing. In both test patterns, each target or stimulus is displayed as a 10-degree-diameter square, with the exception of the central stimulus which is presented as a 5-degree-diameter circle. The 0.25 cycles/degree sinusoidal grating undergoes counterphase flicker at 25 Hz and lasts for 720 msec. There is first a 160 msec increase in contrast, then 400 msec of steady presentation at the set contrast, followed by a 160 msec decrease in contrast. Consecutive stimuli are separated by up to 500 msec of variable pause in order to reduce the rhythmic responses. A button press by the patient between 100 msec and one second after presentation is counted as stimuli detection, at which time the current stimulus will be discontinued in to order to shorten testing time. The original FDT perimeter threshold testing utilizes a four-reversal staircase procedure known as the modified binary search algorithm (MOBS). In this way, contrast is decreased if the stimulus is detected at a higher level, or contrast is increased until a stimulus is detected. Different types of screening protocols are available which vary by contrast level.

The second generation Humphrey Matrix FDT Perimeter tool introduced several new features, including the ability to monitor eye fixation. Threshold testing on the Humphrey Matrix uses smaller targets that are presented along a grid. In addition, greater spatial resolution is available with 24-2, 30-2, 10-2, and macular threshold tests. The 24-2 and 30-2 threshold tests present 5 degree-diameter targets at a higher frequency 0.50 cycles/degree sinusoidal grating that undergoes counterphase flicker at 18 Hz. The 10-2 and macular tests present 2-degree-diameter targets at a counterphase frequency of 12 Hz. The N-30 threshold testing utilizes a two-reversal MOBS algorithm while the other threshold tests unique to the Humphrey Matrix utilize a Bayesian threshold estimation strategy. The 24-2 screening protocol, available on the Humphrey Matrix, utilizes the same principle as the N30 tests but presents 54 targets in a grid bracketing the vertical and horizontal meridians.

During FDT perimetry testing, the patient is presented different flicker targets and instructed to press the response button at the appearance of each stimulus. Due to the relatively large targets used in FDT perimetry, refractive errors up to 6 diopters are not considered to significantly influence test results. Patients can wear their own corrective lenses while performing the test.

As described above, the FDT perimeter can be used for screening or threshold testing. Screening protocols vary by contrast level. Tests with targets at higher contrast levels are more specific for detecting patients with visual field defects while tests with lower contrast levels are more sensitive. Results from FDT perimetry are typically reported using decibels of sensitivity. The FDT perimetry tools incorporate a manufacturer-provided internal normative database. The global indices that are reported are the mean deviation (MD) and pattern standard deviation (PSD). Mean deviation (MD) reports the amount the entire field deviates from normal, and pattern standard deviation (PSD) demonstrates irregularities within the field such as a localized defect.

Other automated perimetry testing tools and strategies can also be used.

For example, the Humphrey visual field analyzer tool, which is sold commercially by Carl Zeiss Meditec, Inc. of Dublin, Calif., employs a number of different testing protocols with different patterns. For example, these patterns include a "10-2" pattern, a "24-2" pattern and a "30-2" pattern. The "10-2" pattern measures 10 degrees temporally and nasally and tests 68 points. It is used for macula, retinal and neuro-ophthalmic conditions and advanced glaucoma. The "24-2" pattern measures 24 degrees temporally and 30 degrees nasally and tests 54 points. It is used for neuro-ophthalmic conditions and general screening as well as early detection of glaucoma. The "30-2" pattern measures 30 degrees temporally and nasally and tests 76 points. It is used for general screening, early glaucoma and neurological conditions. The above tests can be performed in either SITA-Standard or SITA-Fast. SITA-Fast is a quicker method of testing. Prior to commencement of the test, the eye not being tested is patched and the room lights are dimmed. The test type and the eye being tested are selected, and the patient's details are entered, including their refractive error. The Humphrey visual field analyzer tool will provide a lens strength and type (either spherical and/or cylindrical), if required for the test. Before putting the patient onto the machine, the requirements of the test itself are clearly explained. The patient is instructed to maintain fixation on the central target and is given a buzzer to only press when a light stimulus is observed. It is not possible to see every light and some lights appear brighter/duller and slower/faster than others. The patient is positioned appropriately and comfortably against the forehead rest and chin rest. Minor adjustments to the head position are made to center the pupil on the display screen to allow eye monitoring throughout the test. The tool projects a series of white light stimuli of varying intensities (brightness), throughout a uniformly illuminated bowl. The patient uses a handheld button that they press to indicate when a light is observed. This assesses the retina's ability to detect a stimulus at specific points within the visual field. This is called retinal sensitivity and is recorded in 'decibels' (dB). The results are then compared against an age-matched database which highlights unusual and suspicious vision loss, potentially caused by pathology. There are different central fixation targets (including a yellow light, small diamond, and large diamond) that can be used during the test. The fixation target used during the test can be chosen on the basis of the patient's conditions.

These currently available automated perimetry testing tools provide accurate results, but they have a number of disadvantages. More specifically, due to their relatively large size, cost, and logistical requirements (such as the need for an electrical outlet and table), these tools have limited accessibility for community- and internationally-based screenings where high-risk groups without regular access to healthcare stand to benefit.

SUMMARY

An improved visual field perimeter testing tool is provided that employs a head mounted display apparatus configured to removably support a hand-held electronic device comprising at least one processor, memory system and integral display screen. The memory system stores a software program executed by the at least one processor, wherein execution of the software program carries out visual field perimeter testing of a subject wearing the head-mounted display apparatus whereby discrete stimuli are presented to the subject on the display screen of the hand-held electronic device.

In order to address nonlinearity of the display characteristics of the hand-held electronic device, a calibration routine can be performed to generate calibration data that is stored as part of the software program and used to generate the RGB pixel values for the discrete stimuli and background that surrounds the discrete stimuli in a manner that provides accurate contrast sensitivity measurements during the testing.

In embodiments, the visual field perimeter testing tool can further include a remote button that communicates wirelessly with the hand-held electronic device to signal user input events triggered by the subject pressing the remote button. Additionally or alternatively, the head mounted display apparatus can further include an input output module that communicates wirelessly with the hand-held electronic device to signal user input events triggered by the subject interacting with the input output module.

In embodiments, the hand-held electronic device can be smartphone or an e-reader or other hand-held electronic device.

In embodiments, the calibration data can include first calibration data that is used during the execution of the software program to determine at least one RGB value in a corrected RGB color space for a maximum luminance of the discrete stimuli or parts thereof. The corrected RGB color space accounts for nonlinearity in the display characteristics of the display screen for the model smartphone that is executing the software program. In embodiments, the first calibration data can include data representing a two-dimensional fit that relates luminance to RGB and brightness of the display screen for a model of the hand-held electronic device.

In embodiments, the calibration data can include second calibration data that is used during the execution of the software program to determine at least one RGB value in a corrected RGB color space for luminance of a background that surrounds the discrete stimuli, wherein the corrected RGB color space accounts for nonlinearity in the display characteristics of the display screen for the model smartphone that is executing the software program. In embodiments, the second calibration data can represent a lookup table or function that relates RGB corresponding to luminance of a predefined value for the background to brightness of the display screen for the model of the hand-held electronic device.

In embodiments, the discrete stimuli can be periodic functions that are modulated around a background, for example a sinusoidal grating flickered in counterphase.

For the case where the discrete stimuli are periodic functions that are modulated around a background, the calibration data can include third calibration data that is used during the execution of the software program to determine a gamma correction factor. In embodiments, the third calibration data can represent a lookup table or function that relates the gamma correction factor to brightness of the display screen for the model of the hand-held electronic device.

The resulting gamma correction factor can be used during the execution of the software program to convert at least one RGB value in a corrected RGB color space for maximum luminance of the discrete stimuli or parts thereof to a corresponding RGB value in an uncorrected RGB color space. The resulting gamma correction factor can also be used during the execution of the software program to convert at least one RGB value in a corrected RGB color space for luminance of background that surrounds the discrete stimuli to a corresponding RGB value in the uncorrected RGB color space. The execution of the program can be configured to construct RGB pixel values in the uncorrected RGB color space for the discrete stimuli from the at least one RGB value for maximum luminance of the discrete stimuli or parts thereof and the at least one RGB value for luminance of the background in the uncorrected RGB color space. And the execution of the program can be configured to convert or transform the RGB pixel values in the uncorrected RGB color space for the discrete stimuli to RGB pixel values in the corrected RGB color space for the discrete stimuli for display using the gamma correction factor. The corrected RGB color space accounts for nonlinearity in the display characteristics of the display screen for the model smartphone that is executing the software program, while the uncorrected RGB color space does not account for nonlinearity in the display characteristics of the display screen for the model smartphone that is executing the software program.

In embodiments, the execution of the software program can be configured in a screening mode where the discrete stimuli have a limited number of contrast sensitivity values. Additionally or alternatively, the execution of the software program can be configured in a threshold mode where the discrete stimuli have a number of contrast sensitivity values dictated by a staircase adjustment scheme.

DETAILED DESCRIPTION OF THE PREFERRED EMBODIMENTS

Figure 1A:
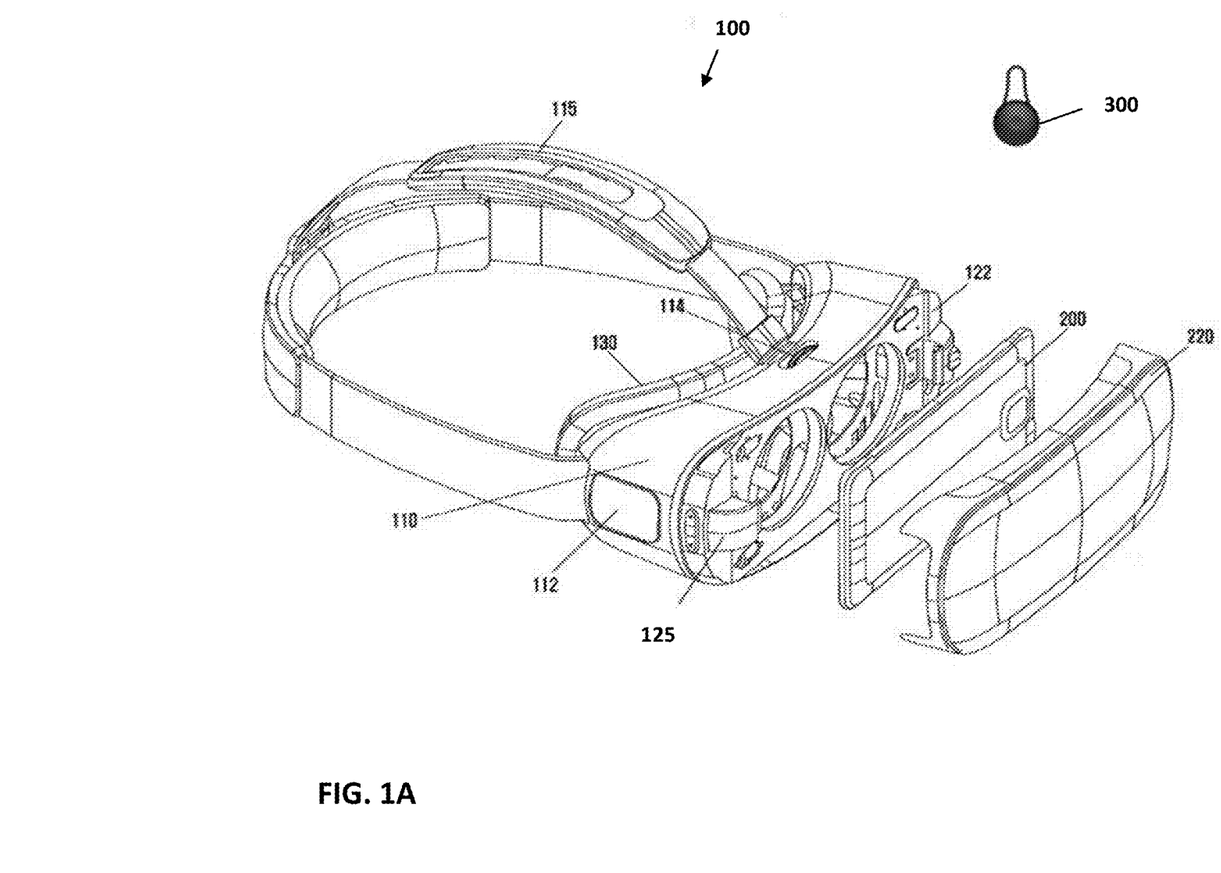
FIG. 1A is a perspective view illustrating the configuration of an exemplary visual field perimetry testing tool according to the present disclosure, where the head-mounted display (HMD) apparatus is shown separated from a hand-held electronic device (e.g., smartphone) and a cover.

FIG. 1A illustrates an embodiment of a visual field perimetry testing tool according to the present disclosure. The three major components of the tool are a head-mounted display (HMD) apparatus 100, a smartphone 200, and a wireless (e.g., Bluetooth) remote button 300 as shown. The HMD apparatus 100 can be configured to support the smartphone 200 in a fixed position in front of the eyes of the subject with its integral display screen facing the eyes of the subject. The smartphone 200 can be configured to present or display discrete targets or stimuli on its integral display screen for testing one or both eyes of the subject. The wireless remote button 300 communicates wirelessly with the smartphone 200 to signal user input events (e.g., button presses) of the remote button 300. The smartphone 200 can be configured to monitor these user input events (e.g., button presses) of the remote button 300. The smartphone 200 can be configured to store and execute a software program (or "app") for visual field perimetry testing as described herein.

The HMD apparatus 100 includes a main frame 110 that can be worn on at least part of the subject's face (e.g., in front of the eyes of the subject) and may be supported in this position through various elements. The front side 122 of the main frame 110 includes a generally planar surface that is sized and shaped to support the smartphone 200 adjacent thereto. The cover 200 is configured to removable engage with the main frame 110 (for example by a snap-fit interface, mechanical coupling, and/or magnetic interface) and ensure the smartphone 200 is positioned in place adjacent the main frame 110 with the display screen of the smartphone 200 facing the main frame 110. In embodiments, the apparatus 100 can include fastening parts 125 that are configured to fix the smartphone 200 in place adjacent the front side 122 of the main frame 110 with the display screen of the smartphone 200 facing the main frame 110.

The main frame 110 has a rear side 130 that has a shape or structure for contacting the subject's face and covering the subject's eyes. The rear side 130 may include a nose recess where the subject's nose is located. The rear side 130 110 can also include a resilient body that contacts the subject's face. The resilient body may be made of at least one cushion material in order to provide a comfortable fit when brought into contact with the subject's face. In embodiments, the resilient body may be detachably coupled to the main frame 110, for example by Velcro tape, an adhesive, etc.

The main frame 110 can support a lens assembly (not shown) that provides optical elements (e.g., lens) in the two optical paths between the subject's left and right eyes and the display screen of the smartphone 200 when the smartphone 200 is supported in place adjacent the front side 122 of the main frame 110. The lens assembly and corresponding optical paths allow the subject to view the display screen of the smartphone when wearing the HMD apparatus 100 of the present disclosure. In embodiments, the apparatus 100 can include a position adjustment mechanism or part 114 that is operated to move the lenses of the assembly along internal rails (not shown) in order to adjust the interpupillary distance of the lenses. In embodiments, the position adjustment part 114 can be configured in the form of a wheel or a dial. The subject (or clinician) may turn the wheel or the dial in order to adjust the interpupillary distance of the lenses.

The main frame 110 may be formed of a material, for example plastic, which is light enough for the subject to perceive wearing comfort and can support the smartphone 200. The main frame 110 may further contain a material for protecting the HMD apparatus 100. For example, the protective material may include at least one of various materials that provide strength and/or beauty. For example, the material may include at least one of the following: glass, plastic (e.g., ABS, polycarbonate, etc.), ceramics, metal (e.g., aluminum), and/or metal alloy (e.g., steel, stainless steel, titanium, or magnesium alloy).

The apparatus 100 can also include a support part 115 (e.g., top and side bands) that is configured to facilitate bringing the rear side 130 of the frame 110 in contact with the subject's face. In embodiments, the length of the support part 115 (or parts thereof) can be adjusted to fit the subject's head. Alternatively, the support part 115 (or part thereof) can be formed by a band of resilient material that adjusts to fit the subject's head. The support part 115 can possibly include cushion material in order to provide a comfortable fit.

In embodiments, the main frame 110 may support a device or user input module 112 together with a suitable communication module (such as a wired USB or wireless Bluetooth module) that can be configured to cooperate to provide user input to the smartphone 200. The device 112 may include, for example, at least one of the touchpad, a physical key, a physical button, a touch key, a joystick, and a wheel key on the side of the main frame 110. The user input module 112 can be configured to provide the user input events (e.g., button presses) in place of the remote button 300 during the visual field testing as described herein.

Note that another suitable HMD apparatus can be used as well.

Figure 1B:
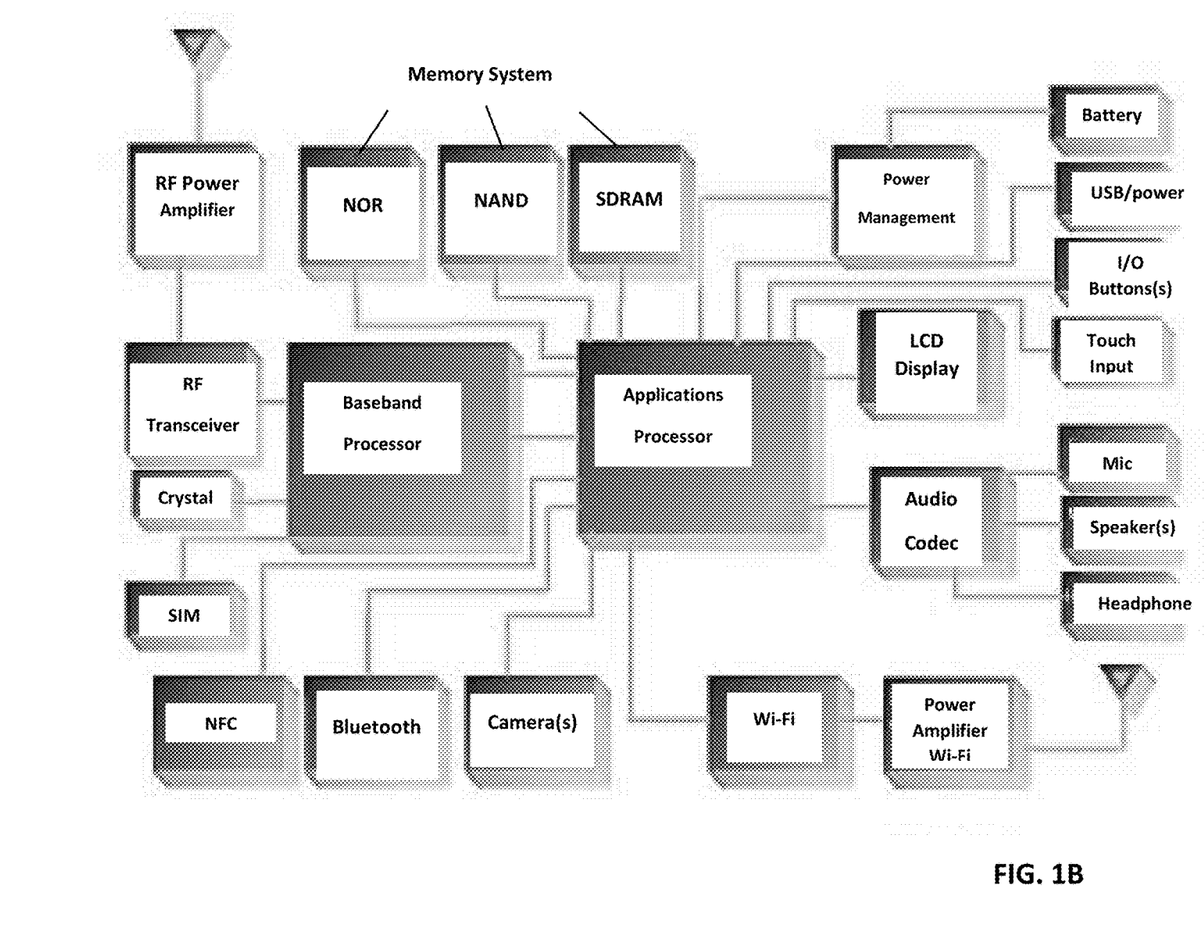
FIG. 1B is a functional block diagram of the components of an exemplary smartphone.

Referring first to FIG. 1B, there is shown a simplified block diagram of part of an exemplary smartphone 200 suitable for use with an HMD apparatus as described herein. The smartphone 200 is a handheld personal computer with a mobile operating system and an integrated mobile broadband cellular network connection for voice, SMS, MMS, and Internet data communication. The smartphone 200 also supports Wi-Fi data communication. The smartphone 200 includes an integral display screen and is capable of executing a variety of computer programs or applications ("apps") that interface with the subject (or clinician) via the integral display screen.

As shown, the smartphone 200 includes a baseband processor, RF transceiver, RF power amplifier. The baseband processor may perform a number of data processing operations and/or signal processing operations at baseband frequencies. The radio frequency (RF) transceiver may perform a number of signal processing operations, such as converting baseband signals from or to RF signals, filtering signals and/or (de)modulating signals. An antenna may be coupled to the RF power amplifier. RF signals may be received from and/or transmitted to a wireless communication channel at the antenna.

The baseband processor, RF transceiver, RF power amplifier and antenna may operate in manner compatible or complying with different communication protocols for communicating voice, SMS, MMS and data. The communication protocol may for example be a second generation (2G) mobile communication protocol (such as CDMA or GSM), a 2.5G mobile communication protocol (such as EGPRS), a 3rd generation mobile communication protocol (such as UMTS or WCDMA), a 4th generation mobile communication protocol (such as Long Term Evolution (LTE) or WiMax), or a 5th generation mobile.

The smartphone 200 also includes an application processor that executes a mobile operating system (such as IOS or Android operating system) that supports applications running in the mobile operating system environment. The application processor provides a self-contained operating environment that delivers all system capabilities needed to support a device's applications, including memory management, graphics processing and multimedia decoding. The applications processor interfaces to a memory system, which can be realized by IC-based non-volatile storage such as NOR memory, NAND memory and SDRAM. The memory system stores the mobile operating system and applications (including the visual field testing application as described herein) that are executed on the applications processor.

The smartphone 200 also includes a wi-fi modem, wi-fi power amplifier and antenna that support wireless communication compliant with one or more IEEE 802.11 communication protocols. The smartphone 200 can also include a Bluetooth module that supports wireless communication compliant with the Bluetooth standard. In other systems, the functionality of the Bluetooth module and the wi-fi modem, wi-fi power amplifier and antenna can be combined together in a single module.

The smartphone 200 can also include an NFC module that supports wireless near field communication, one or more camera, an audio codec that processes audio signals together with a mic input, a headphone output and one or more speakers.

The smartphone 200 can also include a USB module (or Lightning module) and port that provides a wired serial interface to peripheral equipment. The smartphone 200 also includes power management module that interfaces to an internal battery and provides power regulation to supply the various power signals used by the other modules the system. The power management module can also control charging of the battery when external power is supplied via the USB/Lightning port.

The smartphone 200 also includes an integral display screen, which can be an LCD display screen (such TFT LCD or IPS-LCD) or an OLED display screen (such as AMOLED or Super AMOLED display screen). The smartphone 200 can also include a touch input controller for managing touch input (e.g., touches, swipes, pinches, etc.) via user interaction with the display screen. The smartphone 200 can also include other I/O buttons, such an on/off button, volume control button(s), home button and hard reset switch.

The smartphone 200 can also include other modules (not shown), such as a GPS sensor, accelerometers for axis-based motion sensing, a gyroscope for sensing phone orientation, a magnetometer, a barometer, one or infrared emitters (VCSELs) and supporting optics that cooperate with one or more infrared sensors for face recognition and/or possible augmented reality applications.

In embodiments, the smartphone 200 can be a Nexus 5 smartphone (LG Electronics, South Korea), which as a low cost (approximately $100), large display size (4.95"), and high resolution (1080p). The screen size ensures the entire visual field testing area can be displayed. The 1080p resolution can aid in eliminating a screen-door effect when viewing the display screen of the smartphone 200 through the HMD apparatus.

In embodiments, the HMD apparatus can be the BoboVR Z3 virtual reality headset (BoboVR, Shenzhen, China), which is relatively inexpensive (approximately $25) and houses two aspheric lenses (diameter=44 mm, focal length=55 mm). The aspheric lenses minimize peripheral distortion which eliminates the need for software-based distortion correction. The BoboVR Z3 virtual reality headset also has an adjustable interpupillary distance and is wide enough to accommodate most spectacle frames, but testing can be performed on subjects without correction with refractive errors between −6 D and +2 D. Furthermore, the wireless remote button 300 can be a Wireless Bluetooth Camera Remote Control Shutter sold commercially by Yescom USA of City of Industry, Calif., which has a communication distance of 10 ft and is suitable for smartphone models that use Android mobile operating system environment (such as the Nexus 5 smartphone) or an iOS mobile operating system environment (such as iPhone models sold commercially by Apple, Inc. of Cupertino, Calif.).

In alternate embodiments, other programmable hand-held electronic devices, such as a hand-held computer with screen or e-reader device, can be used in place of the smartphone 200.

The software program (or "app") for visual field perimetry testing as executed by the smart phone 200 (or other electronic device) measures the contrast sensitivity in different locations of the retina, reported in decibels. Contrast sensitivity in decibels is derived with the following equation, where C is the contrast:

$$dB = -20 \log_{10}(C) \qquad \text{Eqn. (1)}$$

Depending on the stimulus, one of two equations for contrast may be used. For tests where small features are presented on a large uniform background, such as a Goldmann stimuli similar to the tests carried out by the Humphrey Field Analyzer tool, the Weber contrast can be used and is calculated as follows, where I is the luminance of the stimulus and $I_b$ is the luminance of the background:

$$C_{Weber} = \frac{I - I_b}{I_b} \qquad \text{Eqn. (2)}$$

For tests where stimuli are periodic functions that are modulated around the background, e.g. the frequency doubling tests which use a sinusoidal grating flickered in counterphase, the Michelson contrast can be used and can be calculated as:

$$C_{Michelson} = \frac{I_{max} - I_{ave}}{I_{ave}} \qquad \text{Eqn. (3)}$$

Note that $I_{max}$ is the maximum luminance of the sine grating and Iaw is a fixed luminosity value suitable for background. For example, in embodiments, $I_{ave}$ can be set at 100 cd/m², which is consistent with the Humphrey FDT Matrix tools. Alternatively, Iave can be fixed at some other luminance value suitable for background. For the frequency doubling testing, the Michelson equation can be used to calculate contrast percentages because the stimulus is sinusoidal.

Figure 2:
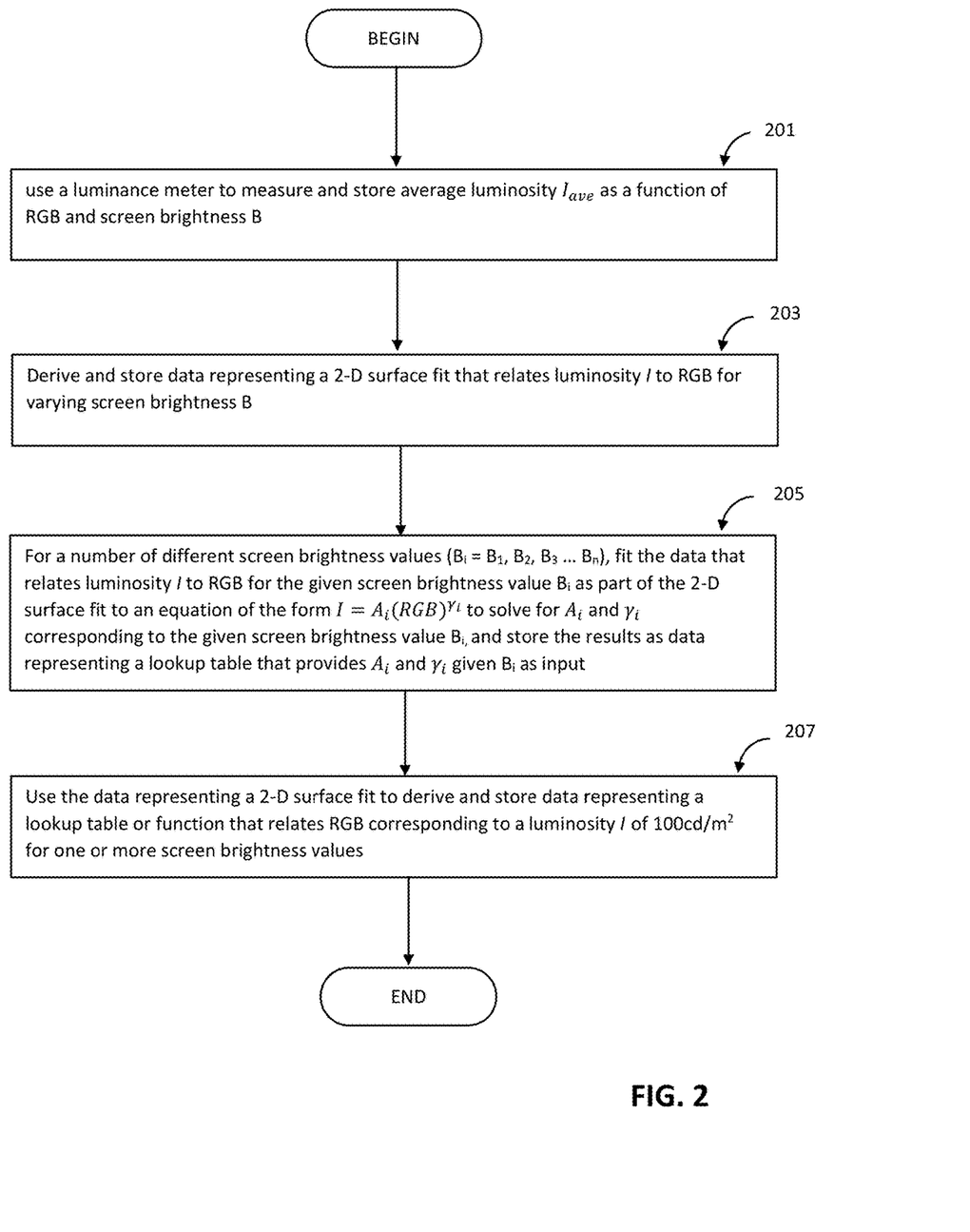
FIG. 2 is a flowchart that illustrates an exemplary calibration routine for generating calibration data for a model of the hand-held electronic device that executes the software program. Such calibration data can be stored as part of the software program and used during execution of the software program to generate the RGB pixel values for the discrete stimuli and background that surrounds the discrete stimuli in a manner that addresses nonlinearity of the display characteristics of the hand-held electronic device and thus provides accurate contrast sensitivity measurements during the testing.

Note that the luminance of the display screen of the smartphone 200 (or other hand-held electronic device) is determined by the brightness and the RGB values of the pixels of the display screen. Because different phone models are made with different screens with varying maximum brightness and other qualities, the relation of luminance to brightness and the RGB values of the pixels is non-linear and varies for different phone models. In order to address these issues and provide accurate contrast sensitivity measurements during the testing, a calibration routine as shown in FIG. 2 can be performed for each model of smartphone (or other electronic device) that executes the software program (or "app") that conducts the visual field perimetry testing as described herein.

The calibration routine begins in block 201 where the RGB value for all pixels of the display screen of the given model of smartphone is varied as a function of screen brightness. For each RGB pixel value and screen brightness B, a luminance meter is used to measure and store the average luminosity $I_{ave}$ of the display screen as a function of the RGB pixel value and the screen brightness B. These measurements can be performed over a number of different units and averaged to provide data representative of all display screens for the given model of smartphone.

Figure 4:
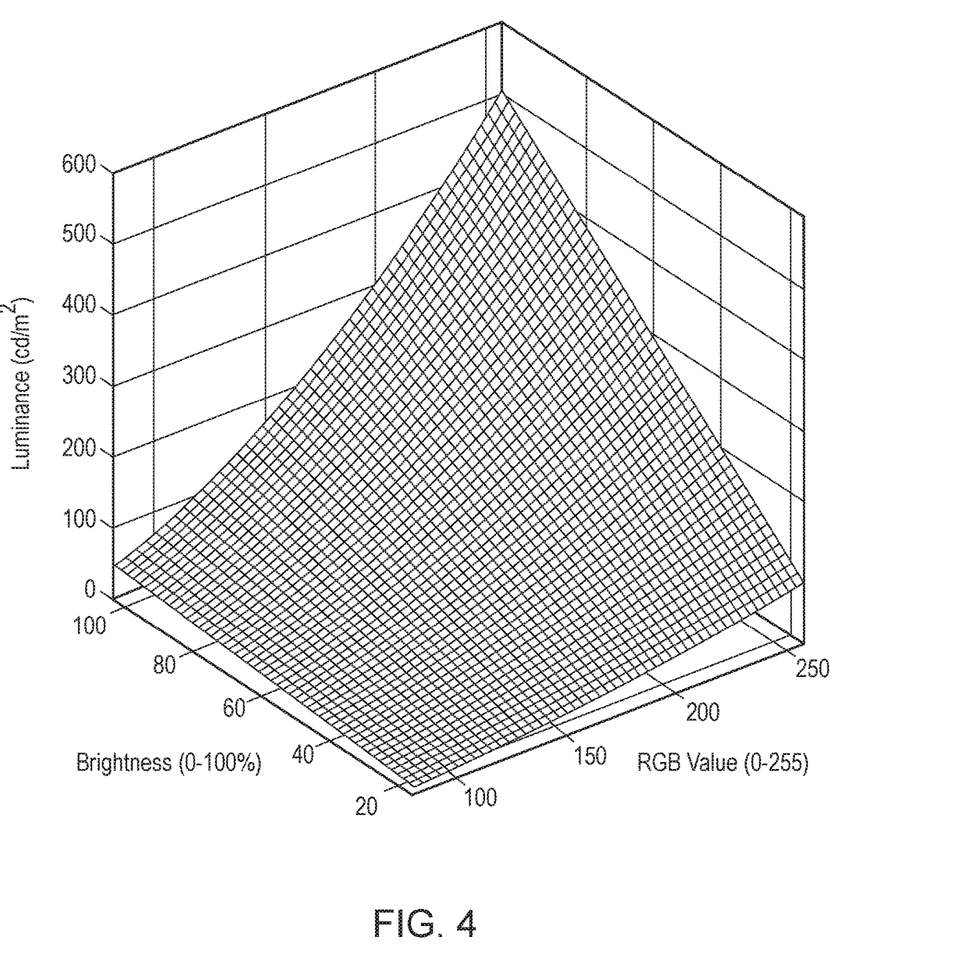
FIG. 4 is a graph of an exemplary two-dimensional (2D) surface fit that can represented by the calibration data generated by the calibration routine of FIG. 2.

In block 203, computer-implemented data processing methods can be used to process the average luminosity $I_{ave}$ of the display screen as a function of the RGB pixel value and the screen brightness B as measured and stored in block 201 in order to derive and store data representing a 2-D surface fit that relates luminosity I to RGB for varying screen brightness B. An example of such a 2-D surface fit is shown in FIG. 4. The data representing the 2-D surface fit provides a luminance value corresponding to the brightness and RGB value of the screen. For example, at 40% brightness, the 183 RGB value corresponds to a luminance of 100 cd/m2.

In block 205, computer-implemented data processing methods can be used over a number of different screen brightness values ($B_i=B_1$, $B_2$, $B_3$ ... $B_n$) to fit the data that relates luminosity I to RGB for the given screen brightness value B as part of the 2-D surface fit of block 203 to an equation of the form $I=A_i(RGB)^{\gamma_i}$ and thus solve for $A_i$ and $\gamma_i$ corresponding to the given screen brightness value $B_i$. These results can be stored as data representing a lookup table that provides $A_i$ and $\gamma_i$ given $B_i$ as input.

In block 207, computer-implemented data processing methods can be used to process the data representing the 2-D surface fit of block 203 to derive and store data representing a lookup table or function that relates RGB corresponding to a luminosity I of 100 cd/m² for one or more screen brightness values. In other embodiments, the calibration data of block 205 can represent a lookup table or function that relates RGB corresponding to a luminosity I of some other value suitable for the background for one or more screen brightness values.

Note that the data produced and stored by blocks 203, 205 and 207 of the calibration process can be integrated as part of the software program (or "app") that conducts the visual field perimetry testing as described herein and thus loaded into the memory system of the given model smartphone. Thus, different phone models can use different calibration data. Such calibration data can be used to provide accurate contrast sensitivity measurements during the testing in a manner that compensates for the nonlinearity of the display screen of the given model of smartphone as well as the differences in display screens between smartphone models.

More specifically, the software program that is executed by a smartphone (or other hand-held electronic device) in conjunction with a HMD apparatus can store and use the calibration data of block 203 to determine at least one RGB value (in a corrected RGB color space) for the maximum luminance of the target stimuli (or parts thereof), and store and use the calibration data of block 207 to determine at least one RGB value (in a corrected RGB color space) for the luminance of the background that surrounds the target stimuli. Note that the corrected RGB color space accounts for nonlinearity in the display characteristics of the display screen for the model smartphone that is executing the software program and thus provides accurate contrast sensitivity for the testing.

Furthermore, for the tests where stimuli are periodic functions that are modulated around the background, e.g. the frequency doubling tests which use a sinusoidal grating flickered in counterphase, the software program that is executed by the smartphone (or other hand-held electronic device) in conjunction with a HMD apparatus can store and use the calibration data of block 205 to determine a gamma correction factor. Such gamma correction factor can be used to convert both at least one RGB value (in the corrected RGB color space) for the maximum luminance of the target stimuli (or parts thereof) and at least one RGB value (in the corrected RGB color space) for the luminance of background that surrounds the target stimuli to corresponding RGB values in an uncorrected RGB color space. The uncorrected RGB color space does not account for nonlinearity in the display characteristics of the display screen for the model smartphone that is executing the software program. The RGB pixel values for the periodic stimuli can then be constructed from the RGB values for the maximum luminance of the target stimuli (or parts thereof) and for the background in the uncorrected RGB color space, and the resulting RGB pixel values for the periodic stimuli can be converted back to the corrected RGB color space using the gamma correction factor for display. In this manner, the periodic target stimuli can be initially constructed in the uncorrected RGB color space and then converted or transformed into the corrected RGB color space for display using the gamma correction factor.

FIGS. 3A-3D is a flowchart of an illustrative software program that is executed by a smartphone (or other hand-held electronic device) in conjunction with a HMD apparatus as described herein to conduct visual field perimetry testing with frequency doubling stimuli.

Figure 3A:
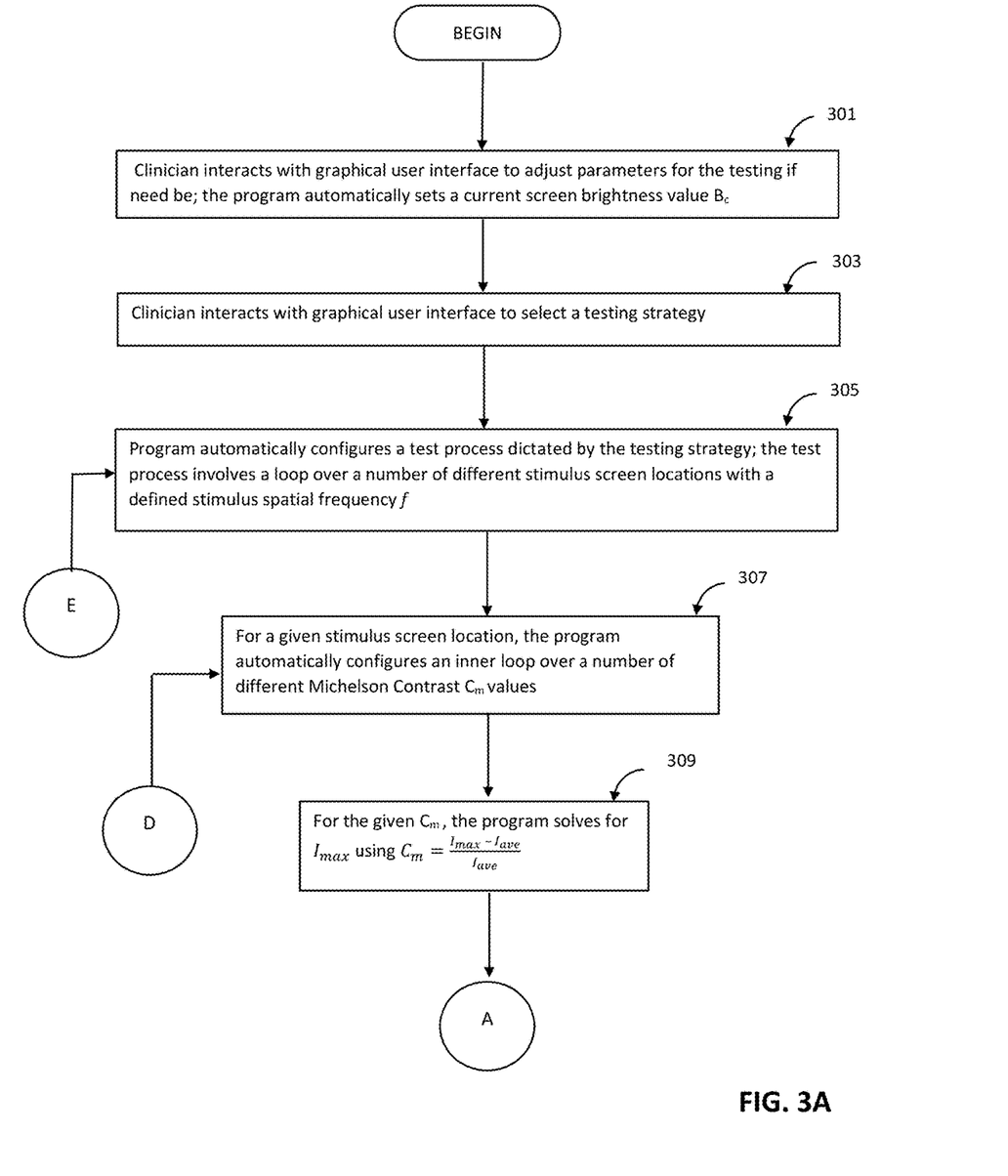
FIGS. 3A-3D, collectively, is a flowchart of an illustrative software program that is executed by a smartphone (or other hand-held electronic device) in conjunction with an HMD apparatus as described herein to conduct visual field perimetry testing with frequency doubling stimuli.

In block 301, the clinician interacts with a graphical user interface presented on the display screen of the smartphone to adjust parameters for the test if need be. Furthermore, the program automatically sets a current screen brightness value $B_c$.

In block 303, the clinician interacts with a graphical user interface presented on the display screen of the smartphone to select a testing strategy (for example, a particular pattern and/or mode (such as a screening mode or threshold mode for a pattern).

In block 305, the program automatically configures a test process dictated by the testing strategy. The test process involves a loop over a number of different stimulus screen locations with a defined stimulus spatial frequency f. For example, if a C-20 pattern in screening mode is selected, the test process can involve sixteen 10°×10° targets or stimuli (at sixteen different screen locations) and one central, circular 5° diameter target in the central 20° of visual field. Note that the stimulus spatial frequency f can be fixed by design or set by user input or configuration.

In block 307, for a given stimulus screen location, the program can configure an inner loop over a number of different Michelson Contrast $C_m$ values. The inner loop can be used for threshold mode testing or screening mode testing if desired. In the screening mode testing, the inner loop can iterate over a limited number of Michelson Contrast $C_m$ values, which can be based on the patient's age determined by an internal normative database as is well known. In embodiments, three contrast levels can be used at varying statistical significance. For example, if a patient doesn't see the first contrast in a given location, it is assumed their contrast sensitivity in that location is worse than, for example, 1% of the population (for a p<0.01), then they are tested at a contrast sensitivity corresponding to p<0.025 and p<0.05. In the threshold mode testing, the inner loop can iterate over a number of Michelson Contrast $C_m$ values dictated by a staircase adjustment scheme as is well known.

In block 309, for the given Michelson Contrast $C_m$ value, the program solves for $I_{max}$ using Eq. (3).

In block 311, the program automatically determines a gamma $\gamma_c$ that corresponds to $B_c$. In embodiments, gamma $\gamma_c$ can be determined using the calibration data of block 205 for the model smartphone that is executing the program. Such calibration data represents a lookup table that provides $A_i$ and $\gamma_i$ given $B_i$ for the model smartphone that is executing the program. The current brightness value $B_c$ (or one or more values close to current brightness value $B_c$) can be used as an input to the lookup table of block 205 to select or interpolate $\gamma_i$ for $B_i$ ($B_1$, $B_2$, $B_3$ ... $B_n$) equal to or closest to $B_c$ to determine the corresponding value of $\gamma_c$.

In block 313, the program determines an RGB value (in the corrected RGB color space) corresponding to $I_{max}$ of 309 for the given $B_c$, which is referred to as $RGB_{I_{max},corrected}$. In embodiments, $RGB_{I_{max},corrected}$ can be determined using the calibration data of block 203 for the model smartphone that is executing the program. Such calibration data represents a 2-D surface fit that relates luminosity I to RGB for varying screen brightness B. The current brightness value $B_c$ (or one or more values close to current brightness value $B_c$) and luminosity $I_{max}$ as determined in 309 can be used as an input to the 2-D surface fit to determine the corresponding RGB value. This determination can be based on selection or interpolation of the RGB value(s) corresponding to a luminosity $I_{max}$ for $B_i$ equal to or closest to $B_c$.

Figure 3B:
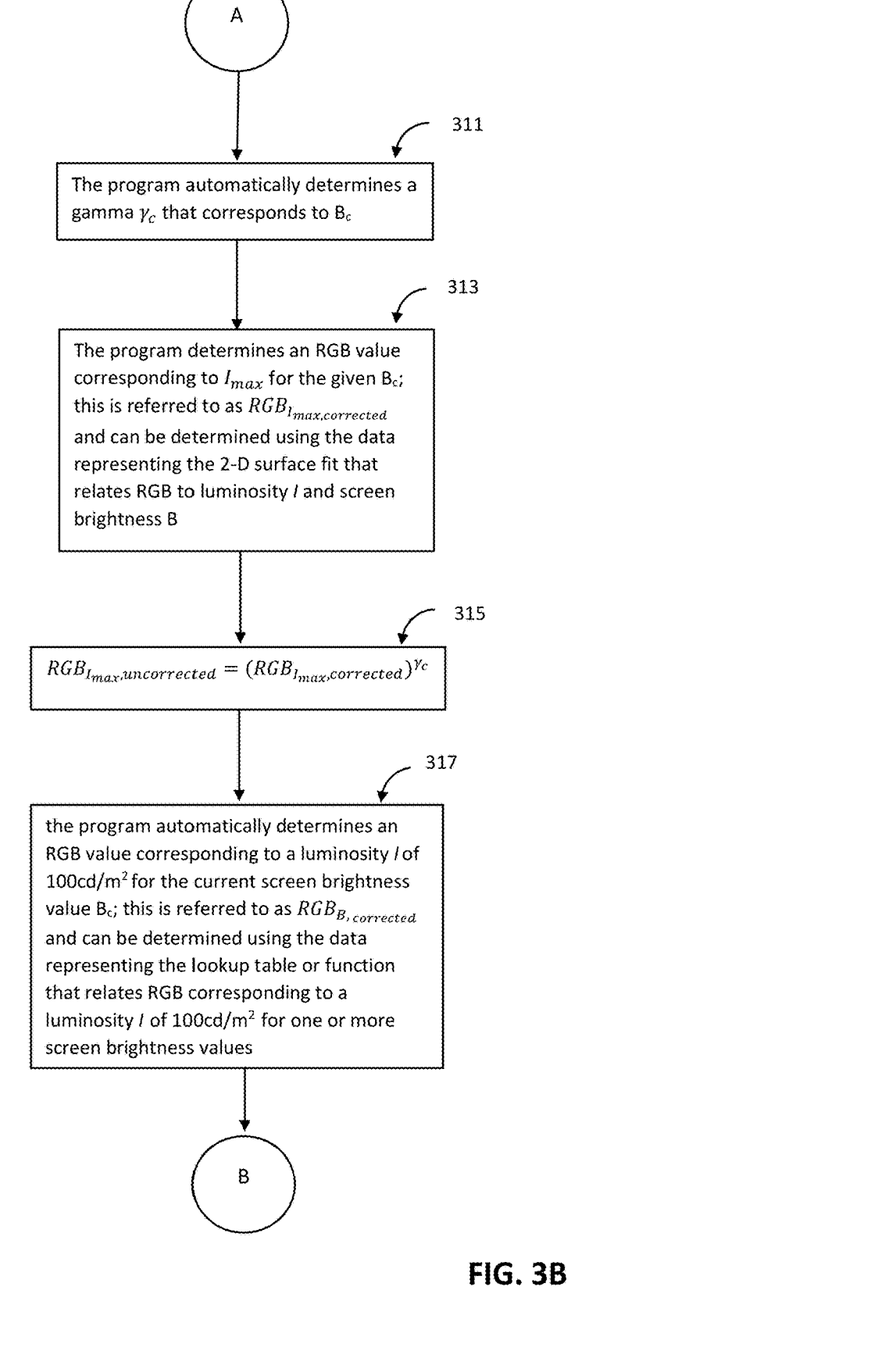

In block 315, the program uses gamma $\gamma_c$ as determined in 311 to convert $RGB_{I_{max},corrected}$ to a corresponding RGB value (in the uncorrected RGB color space), which is referred to $RGB_{I_{max},uncorrected}$. In embodiments, such correction can be calculated as:

$$RGB_{I_{max},uncorrected} = (RGB_{I_{max},corrected})^{\gamma_c} \qquad \text{Eqn. (4)}$$

In block 317, the program automatically determines an RGB value (in the corrected RGB color space) corresponding to a luminosity/of 100 cd/m² for the current screen brightness value $B_c$, which is referred to as $RGB_{B,corrected}$. In embodiments, $RGB_{B,corrected}$ can be determined using the calibration data of block 207 for the model smartphone that is executing the program. Such calibration data represents a lookup table or function that relates RGB corresponding to a luminosity I of 100 cd/m² for one or more screen brightness values. The current brightness value $B_c$ (or one or more values close to current brightness value $B_c$) can be used as an input to lookup table or function to determine the corresponding RGB value. This determination can be based on selection or interpolation of RGB value(s) for the & equal to or closest to $B_c$ to determine the corresponding RGB value. In other embodiments, the calibration data of block 205 can represent a lookup table or function that relates RGB corresponding to a luminosity I of some other value suitable for the background for one or more screen brightness values. In this case, the current brightness value $B_c$ (or one or more values close to current brightness value $B_c$) can be used as an input to lookup table or function to determine the corresponding $RGB_{B,corrected}$ for the background.

In block 319, the program uses gamma $\gamma_c$ as determined in 311 to convert $RGB_{B,corrected}$ to a corresponding RGB value (in the uncorrected RGB color space), which is referred to $RGB_{B,uncorrected}$. In embodiments, such correction can be calculated as:

$$RGB_{B,uncorrected} = (RGB_{B,corrected})^{\gamma_c} \qquad \text{Eqn. (5)}$$

In block 321, the program automatically solves for A as:

$$A = RGB_{I_{max},uncorrected} - RGB_{B,uncorrected} \qquad \text{Eqn. (6)}$$

Figure 3C:
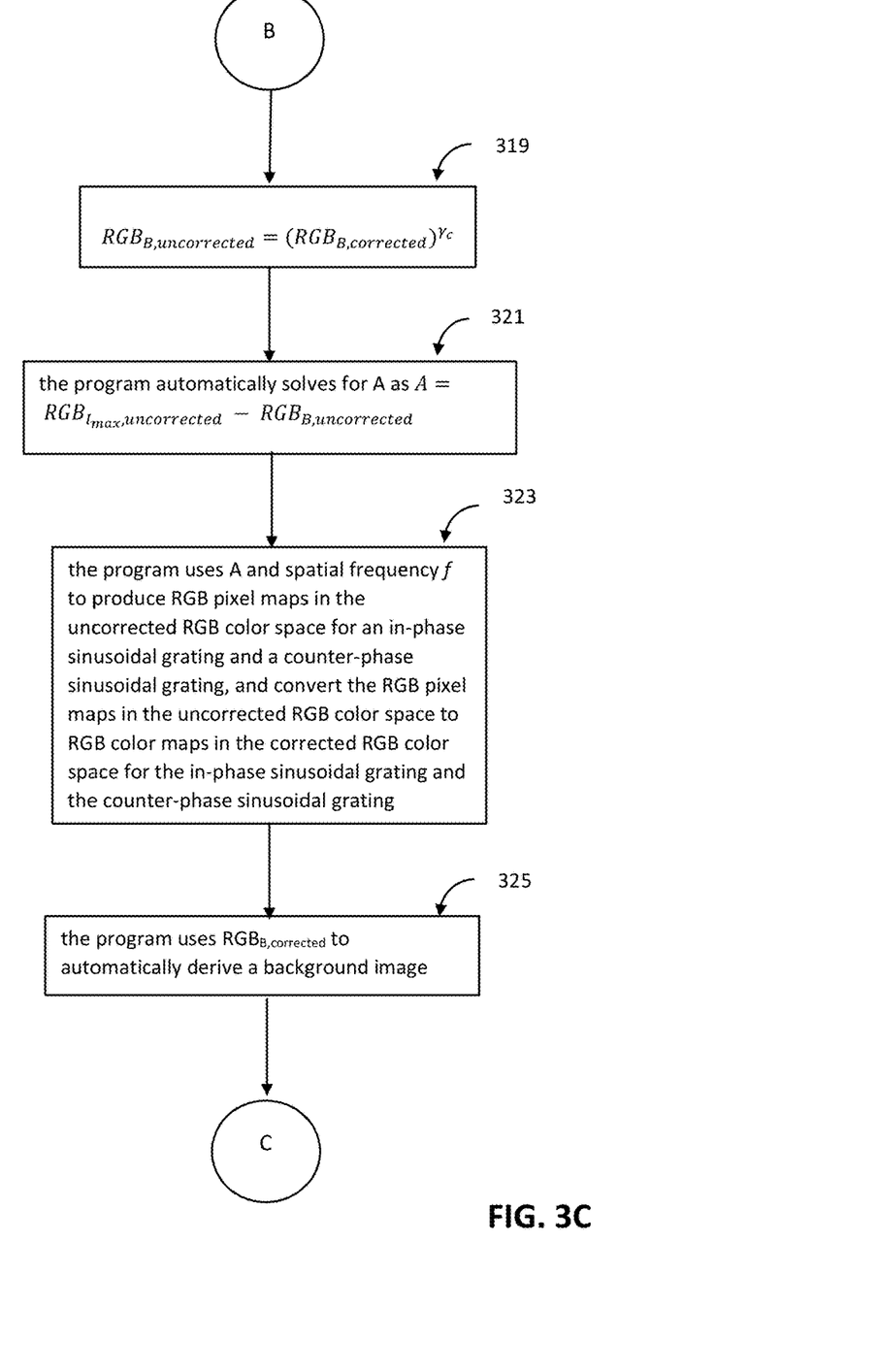

In block 323, the program uses A as determined in block 321 and the spatial frequency f to produce RGB pixel maps in the uncorrected RGB color space for an in-phase sinusoidal grating and a counter-phase sinusoidal grating, and convert the RGB pixel maps in the uncorrected RGB color space to RGB color maps in the corrected RGB color space for the in-phase sinusoidal grating and the counter-phase sinusoidal grating.

For example, the in-phase sinusoidal grating and the counter-phase sinusoidal grating both employ 100×100 pixel map with 100 pixels in the x-direction and 100 pixels in the y direction where $x_i$ are pixel indices in the range of 1 to 100 ($x_{max}$) and $y_i$ are pixel indices in the range of 1 to 100 ($y_{max}$) in they direction. In this case, a loop can be performed each pixel index $x_i$ in the x direction. For the current pixel index $x_i$, $RGB_{IP\ at\ x_i,uncorrected}$ can be calculated as:

$$RGB_{IP\ at\ x_i,uncorrected} = A\sin(2f^{x_i}/x_{max}+\pi/2) + RGB_{B,uncorrected} \qquad \text{Eqn. (7a)}$$

And $RGB_{IP\ at\ x_i,uncorrected}$ can be converted $RGB_{IP\ at\ x_i,corrected}$ using gamma $\gamma_c$ as determined in 311 as:

$$RGB_{IP\ at\ x_i,corrected} = (RGB_{IP\ at\ x_i,uncorrected})^{1/\gamma_c} \qquad \text{Eqn. (7b)}$$

For the RGB pixel map of the in-phase sinusoidal grating, $RGB_{IP\ at\ x_i,corrected}$ can be set as the RGB value for each pixel in the column of pixels at the current pixel index $x_i$. Furthermore, for the current pixel index $x_i$, $RGB_{CP\ at\ x_i,uncorrected}$ can be calculated as:

$$RGB_{CP\ at\ x_i,uncorrected} = A\sin(2f^{x_i}/x_{max}+3\pi/2) + RGB_{B,uncorrected} \qquad \text{Eqn. (7c)}$$

And $RGB_{CP\ at\ x_i,uncorrected}$ can be corrected to $RGB_{CP\ at\ x_i,corrected}$ using gamma $\gamma_c$ as determined in 311 as:

$$RGB_{CP\ at\ x_i,corrected} = (RGB_{CP\ at\ x_i,uncorrected})^{1/\gamma_c} \qquad \text{Eqn. (7d)}$$

For the RGB pixel map of the counter-phase sinusoidal grating, $RGB_{CP\ at\ x_i, corrected}$ can be set as the RGB value for each pixel in the column of pixels at the current pixel index $x_i$.

In block 325, the program uses to $RGB_{B, corrected}$ as determined in block 317 to automatically derive a background image.

Figure 3D:
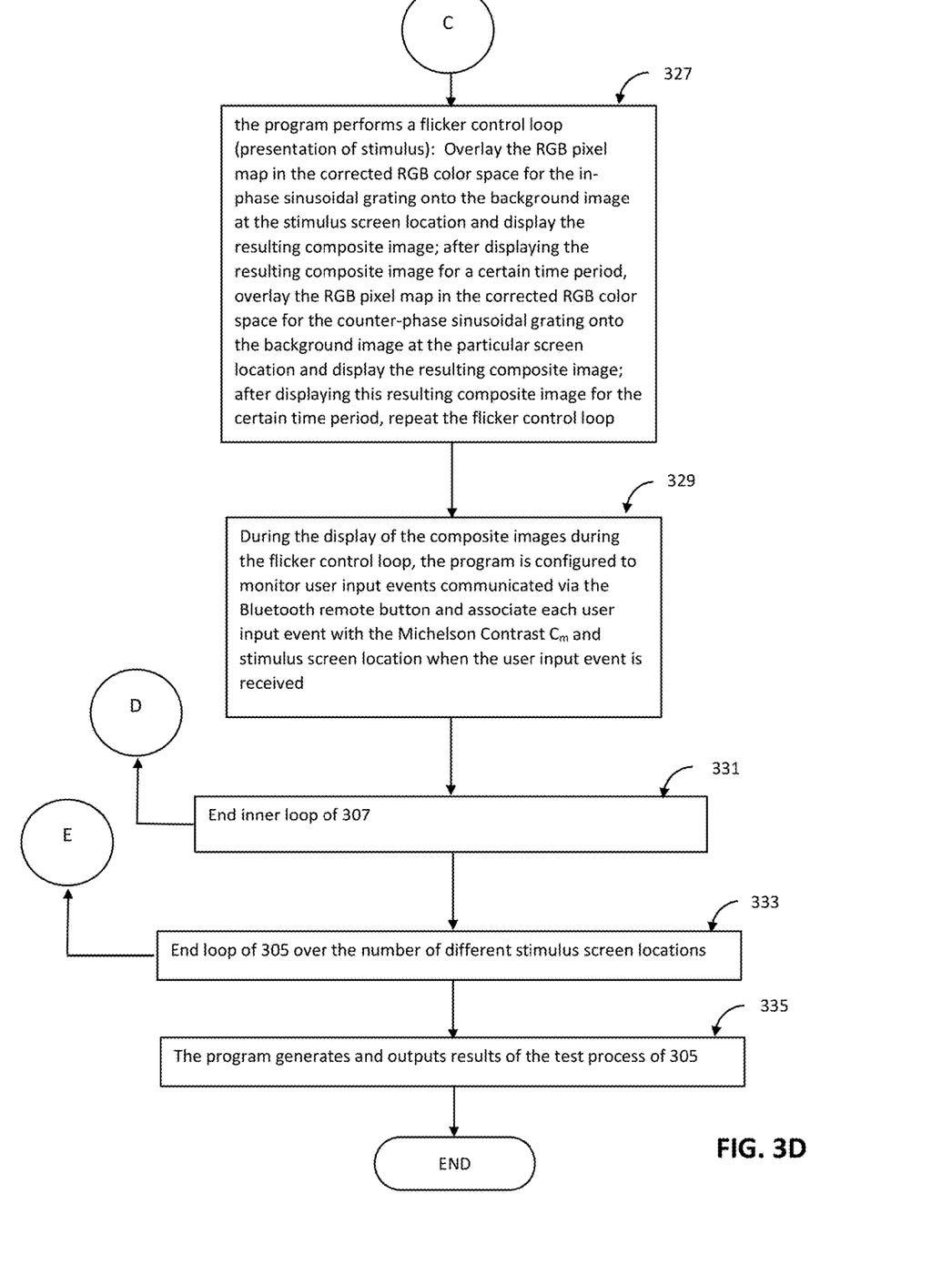

In block 327, the program automatically performs a flicker control loop (presentation of stimulus). Such operations overlay the RGB pixel map in the corrected RGB color space for the in-phase sinusoidal grating as produced in block 323 onto the background image produced in block 325 at the current stimulus screen location (in the configuration, the background surrounds the in-phase sinusoidal grating) and displays the resulting composite image. After displaying the resulting composite image for a certain time period, the RGB pixel map in the corrected RGB color space for the counter-phase sinusoidal grating as produced in block 323 is overlaid onto the background image as produced in block 325 at the particular screen location (in the configuration, the background surrounds the counter-phase sinusoidal grating) and then the resulting composite image is displayed. After displaying this resulting composite image for the certain time period, the flicker control loop is repeated until expiration or termination of the testing with regard the frequency doubling stimulus at the particular stimulus screen location.

In block 329, during the display of the composite images during the flicker control loop of block 327, the program is configured to monitor user input events communicated via the Bluetooth remote button and associate each user input event with the Michelson Contrast $C_m$ and the stimulus screen location when the user input event is received.

In block 331, the program determines if the inner loop of 307 ends. If not, the operations return to 307 to repeat the inner loop of 307 to 329 for another Michelson Contrast $C_m$ value. If so, the operations continue to block 333.

In block 333, the program determines if the loop of 305 ends. If not, the operations return to 305 to repeat the loop of 305 to 331 for another stimulus screen location. If so, the operations continue to 335.

In block 335, the program generates and outputs results of the test process of 305. Such results are based on the Michelson Contrast $C_m$ and the stimulus screen location when the user input events are received over the test process.

In embodiments, the software program that is executed to conduct the visual field perimetry testing utilizes frequency doubling stimuli developed for Android in Java and OpenGL using Android Studio (Google, Mountain View, Calif.). The C-20 screening visual field protocol, which tests sixteen 10°×10° targets and one central, circular 5° diameter target in the central 20° of visual field, can be used if desired. Contrast of the stimuli during each presentation can be adapted from an age-adjusted normative study if desired.

Note that the frequency doubling stimuli can be embodied by sinusoidal gratings programmed at a spatial frequency of 0.25 cycles/degree displayed with a counterphase flicker at 30 Hz for a total of 400 ms. Note that the Humphrey Zeiss FDT uses a flicker frequency of 25 Hz, but as most smartphones operate at a screen refresh rate of 60 Hz, 30 Hz can be used for the application. For each stimulus presentation, the contrast is steadily increased during first 50 ms, displayed 138 for 300 ms, and then steadily decreased during the last 50 ms to avoid temporal transients. Consecutive stimuli are separated by 1100 ms with a variable pause up to 500 ms to reduce rhythmic responses.

In embodiments, the HMD apparatus 100 can be sterilized with alcohol before each subject test. Subjects can be instructed to keep both eyes open and are presented with a stereoscopic view of the fixation target and testing area. Stimuli are presented monocularly and subjects cannot discern which eye is being tested, which is simpler than the Zeiss FDT which requires shifting the eyepiece between eyes and interrupting the test. Fixation is monitored with the Heijl-Krakau method. False positive trials are interspersed throughout the exam to measure reliability. Button presses recorded between 100 ms and 1000 ms after stimulus presentation are counted as a response. Two testing modes can be used: screening and threshold.

In the screening mode, suprathreshold stimuli are shown in each location in a random order at an age-adjusted base contrast. If a button press is correctly captured for a stimulus location, the location is no longer shown. If missed twice, the contrast at that location is increased and shown again at random, and if missed three times, the contrast is further increased and shown again at random. If missed four times, the location is no longer tested. Stimuli seen on the first or second presentation at base contrast are considered normal. Stimuli seen on the third presentation are considered mild defects; stimuli seen on the fourth presentation are considered moderate defects; and stimuli not seen at all are considered severe defects.

In the threshold mode, the contrast sensitivity in each location can be determined using a 4-2 dB staircase with two reversals. The user interface prompts entry of a patient ID, birth-date, test type, and eyes to be tested. Results can be shown on a summary screen and can be saved for later viewing according to a patient's unique ID in a 256-bit AES encrypted database, ensuring HIPAA compliance. An interface to search and view prior exam results can be provided, and results can be exported or printed wirelessly as well.

Advantageously, the tools and methods that perform visual field perimetry testing as described are portable and very cost-effective. Thus, such tools have the potential to make glaucoma screening practices more accessible, especially in resource poor settings. Furthermore, such tools can possible provide for earlier detection of primary open angle glaucoma (POAG), which would allow for earlier intervention and possibly reduce the risk of permanent vision loss.

Certain embodiments as described herein can include logic or a number of components, modules, or mechanisms. Modules may constitute either software modules (e.g., code embodied (1) on a non-transitory machine-readable medium or (2) in a transmission signal) or hardware-implemented modules. A hardware-implemented module is tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In various embodiments, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" should be understood to encompass a tangible entity, be that an entity that is physically constructed, permanently configured (e.g., hardwired) or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules may provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and store the output of that operation in a memory device to which it is communicatively coupled. A further hardware-implemented module may then, at a later time, access the memory device to retrieve and process the stored output. Hardware-implemented modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program may be written in any form of programming language, including compiled or interpreted languages, and it may be deployed in any form, including as a stand-alone program or as a module, subroutine, or other unit suitable for use in a computing environment. A computer program may be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations may also be performed by, and apparatus of example embodiments may be implemented as, special purpose logic circuitry, e.g., a field programmable gate array (FPGA) or an application-specific integrated circuit (ASIC).

The computing system may include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

The term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding, or carrying a set of instructions for execution by the machine and that cause the machine to perform any of the one or more of the methodologies illustrated herein. The term "machine-readable medium" shall accordingly be taken to include, but not be limited to, solid-state memories, and optical and magnetic medium.

Method embodiments illustrated herein may be computer-implemented. Some embodiments may include computer-readable media encoded with a computer program (e.g., software), which includes instructions operable to cause an electronic device to perform methods of various embodiments. A software implementation (or computer-implemented method) may include microcode, assembly language code, or a higher-level language code, which further may include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, Random Access Memories (RAMs), Read Only Memories (ROMs), and the like.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a non-exclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

There have been described and illustrated herein embodiments of tools and methods that perform visual field perimetry testing with of head-mounted display technology. While particular embodiments of the invention have been described, it is not intended that the invention be limited thereto, as it is intended that the invention be as broad in scope as the art will allow and that the specification be read likewise. Moreover, while particular configurations have been disclosed, it will be appreciated that other configurations could be used as well. It will therefore be appreciated by those skilled in the art that yet other modifications could be made to the provided invention without deviating from its spirit and scope as claimed.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. A visual field perimeter testing tool comprising:
   a head mounted display apparatus configured to removably support a hand-held electronic device comprising at least one processor, memory system and integral display screen;
   wherein the memory system of the hand-held electronic device stores instructions executed by the at least one processor, wherein execution of the instructions carries out visual field perimeter testing of a subject wearing the head-mounted display apparatus whereby discrete stimuli are presented to the subject on the display screen of the hand-held electronic device; and
   wherein the memory system of the hand-held electronic device further stores calibration data that is used during the execution of the instructions to determine RGB values for the discrete stimuli or parts thereof in a corrected RGB color space that accounts for nonlinearity in the display characteristics of the display screen of the hand-held electronic device.

2. A visual field perimeter testing tool according to claim 1, further comprising:
   a remote button that communicates wirelessly with the hand-held electronic device to signal user input events triggered by the subject pressing the remote button.

3. A visual field perimeter testing tool according to claim 1, wherein:
   the head mounted display apparatus further comprises an input output module that communicates wirelessly with the hand-held electronic device to signal user input events triggered by the subject interacting with the input output module.

4. A visual field perimeter testing tool according to claim 1, wherein:
   the hand-held electronic device comprises a smartphone.

5. A visual field perimeter testing tool according to claim 1, wherein:
   the calibration data stored by memory system of the hand-held electronic device includes first calibration data that is used during the execution of the instructions to determine at least one RGB value in the corrected RGB color space for a maximum luminance of the discrete stimuli or parts thereof.

6. A visual field perimeter testing tool according to claim 5, wherein:
the first calibration data comprises data representing a two-dimensional fit that relates luminance to RGB and brightness of the display screen for a model of the hand-held electronic device.

7. A visual field perimeter testing tool according to claim 1, wherein:
the calibration data stored by memory system of the hand-held electronic device includes second calibration data that is used during the execution of the instructions to determine at least one RGB value in the corrected RGB color space for luminance of a background that surrounds the discrete stimuli.

8. A visual field perimeter testing tool according to claim 7, wherein:
the second calibration data comprises a lookup table or function that relates RGB corresponding to luminance of a predefined value for the background to brightness of the display screen for a model of the hand-held electronic device.

9. A visual field perimeter testing tool according to claim 1, wherein:
the discrete stimuli are periodic functions that are modulated around a background.

10. A visual field perimeter testing tool according to claim 9, wherein:
the discrete stimuli comprise a sinusoidal grating flickered in counterphase.

11. A visual field perimeter testing tool according to claim 1, wherein:
the calibration data stored by memory system of the hand-held electronic device includes third calibration data that is used during the execution of the instructions to determine a gamma correction factor related to an uncorrected RGB color space that does not account for nonlinearity in the display characteristics of the display screen for the hand-held electronic device;
the resulting gamma correction factor is used during the execution of the instructions to convert at least one RGB value in the corrected RGB color space for maximum luminance of the discrete stimuli or parts thereof to a corresponding RGB value in the uncorrected RGB color space;
the resulting gamma correction factor is used during the execution of the instructions to convert at least one RGB value in the corrected RGB color space for luminance of background that surrounds the discrete stimuli to a corresponding RGB value in the uncorrected RGB color space;
the execution of the instructions constructs RGB pixel values in the uncorrected RGB color space for the discrete stimuli from the at least one RGB value for maximum luminance of the discrete stimuli or parts thereof and the at least one RGB value for luminance of the background in the uncorrected RGB color space; and
the resulting gamma correction factor is used during the execution of the instructions to convert or transform the RGB pixel values in the uncorrected RGB color space for the discrete stimuli to RGB pixel values in the corrected RGB color space for the discrete stimuli for display.

12. A visual field perimeter testing tool according to claim 11, wherein:
the third calibration data comprises a lookup table or function that relates the gamma correction factor to brightness of the display screen for a model of the hand-held electronic device.

13. A visual field perimeter testing tool according to claim 1, wherein:
the execution of the instructions is configured in a screening mode where the discrete stimuli have a limited number of contrast sensitivity values.

14. A visual field perimeter testing tool according to claim 1, wherein:
the execution of the instructions is configured in a threshold mode where the discrete stimuli have a number of contrast sensitivity values dictated by a staircase adjustment scheme.

15. A method for visual field perimeter testing of a subject, comprising:
providing a head mounted display apparatus configured to removably support a hand-held electronic device comprising at least one processor, memory system and integral display screen, wherein the memory system stores instructions; and
controlling the at least one processor to execute the instructions, wherein execution of the instructions presents discrete stimuli to the subject on the display screen of the hand-held electronic device;
wherein the memory system of the hand-held electronic device stores calibration data that is used during the execution of the instructions to determine RGB values for the discrete stimuli or parts thereof in a corrected RGB color space that accounts for nonlinearity in the display characteristics of the display screen of the hand-held electronic device.

16. A method according to claim 15, further comprising:
communicating wirelessly with the hand-held electronic device to signal user input events triggered by the subject.

17. A method according to claim 15, wherein:
the hand-held electronic device comprises a smartphone.

18. A method according to claim 15, wherein:
the calibration data stored by memory system of the hand-held electronic device includes first calibration data that is used during the execution of the instructions to determine at least one RGB value in the corrected RGB color space for a maximum luminance of the discrete stimuli or parts thereof.

19. A method according to claim 18, wherein:
the first calibration data is determined by performing a calibration routine for a model of the hand-held electronic device, wherein the first calibration data comprises data representing a two-dimensional fit that relates luminance to RGB and brightness of the display screen for the model of the hand-held electronic device.

20. A method according to claim 15, wherein:
the calibration data stored by memory system of the hand-held electronic device includes second calibration data that is used during the execution of the instructions to determine at least one RGB value in the corrected RGB color space for luminance of a background that surrounds the discrete stimuli.

21. A visual field perimeter testing tool according to claim 20, wherein:
the second calibration data is determined by performing a calibration routine for a model of the hand-held electronic device, wherein the second calibration data represents a lookup table or function that relates RGB for luminance of a predefined value for the background to brightness of the display screen for the model of the hand-held electronic device.

22. A method according to claim 15, wherein:
the discrete stimuli are periodic functions that are modulated around a background.

23. A method according to claim 22, wherein:
the discrete stimuli comprise a sinusoidal grating flickered in counterphase.

24. A method according to claim 15, wherein:
the calibration data stored by memory system of the hand-held electronic device includes third calibration data that is used during the execution of the instructions to determine a gamma correction factor related to an uncorrected RGB color space that does not account for nonlinearity in the display characteristics of the display screen for the hand-held electronic device.

25. A method according to claim 24, wherein:
the third calibration data is determined by performing a calibration routine for a model of the hand-held electronic device, wherein the third calibration data represents a lookup table or function that relates gamma correction factor to brightness of the display screen for the model of the hand-held electronic device.

26. A method according to claim 24, wherein:
the resulting gamma correction factor is used during the execution of the instructions to convert at least one RGB value in a corrected RGB color space for maximum luminance of the discrete stimuli or parts thereof to a corresponding RGB value in the uncorrected RGB color space;

the resulting gamma correction factor is used during the execution of the instructions to convert at least one RGB value in a corrected RGB color space for luminance of background that surrounds the discrete stimuli to a corresponding RGB value in the uncorrected RGB color space;

the execution of the instructions constructs RGB pixel values in the uncorrected RGB color space for the discrete stimuli from the at least one RGB value for maximum luminance of the discrete stimuli or parts thereof and the at least one RGB value for luminance of the background in the uncorrected RGB color space; and the resulting gamma correction factor is used during the execution of the instructions to convert or transform program converts or transforms the RGB pixel values in the uncorrected RGB color space for the discrete stimuli to RGB pixel values in the corrected RGB color space for the discrete stimuli for display.

27. A method according to claim 15, wherein:
the execution of the instructions is configured in a screening mode where the discrete stimuli have a limited number of contrast sensitivity values.

28. A method according to claim 15, wherein:
the execution of the instructions is configured in a threshold mode where the discrete stimuli have a number of contrast sensitivity values dictated by a staircase adjustment scheme.

* * * * *